US006048535A

United States Patent [19]

Sharma

[11] Patent Number: 6,048,535
[45] Date of Patent: *Apr. 11, 2000

[54] MULTIVALENT IN OVO AVIAN VACCINE

[75] Inventor: Jagdev M. Sharma, Vadnais Heights, Minn.

[73] Assignee: Regents of the University of Minnesota, Minneapolis, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/874,103

[22] Filed: Jun. 12, 1997

[51] Int. Cl.$^7$ .................. A61K 39/295; A61K 39/12; A61K 39/15; A01N 63/00

[52] U.S. Cl. .................. 424/202.1; 424/199.1; 424/201.1; 424/204.1; 424/214.1; 424/215.1; 424/216.1; 424/232.1; 424/229.1; 424/93.6; 424/816

[58] Field of Search .................. 424/199.1, 201.1, 424/202.1, 204.1, 214.1, 215.1, 222.1, 216.1, 229.1, 232.1, 93.6, 816

[56] References Cited

U.S. PATENT DOCUMENTS

| | | | |
|---|---|---|---|
| 4,040,388 | 8/1977 | Miller | 119/1 |
| 4,458,630 | 7/1984 | Sharma et al. | 119/1 |
| 5,470,734 | 11/1995 | Sondermeijer et al. | 435/235.1 |
| 5,525,342 | 6/1996 | Rosenberger | 424/202.1 |
| 5,686,287 | 11/1997 | Baxendale | 424/299.1 |
| 5,733,554 | 3/1998 | Audonnet et al. | 424/199.1 |
| 5,733,556 | 3/1998 | Schrier | 424/214.1 |
| 5,750,101 | 5/1998 | Stone | 424/85.2 |

FOREIGN PATENT DOCUMENTS

WO95/35121 12/1995 WIPO.

OTHER PUBLICATIONS

Sharma, J.M., "Embryo vaccination of specific–pathogen–free chickens with infectious bursal disease virus: tissue distribution of the vaccine virus and protection of hatched chickens against disease", *Avian Diseases*, vol. 30, No. 4, 776–780, (Apr. 21, 1986).

Stone, H., et al., "In ovo vaccination of chicken embryos with experimental Newcastle Diseases and avian influenza oil–emulsion vaccines", vol. 41 vol. 41, 856–863, (1997).

Waknell, P.S., et al., "Chicken embryonal vaccination with avian infectious bronchitis virus", *American Journal of Veterinary Research*, vol. 47, No. 4, 933–938, (Apr. 1986).

Reddy, S.K. et al., "Protective Efficacy of a Recombinant Herpesvirus of Turkeys as an in ovo Vaccine Against Newcastle and Marek's Diseases in Specific–Pathogen–Free Chickens", *Vaccine*, vol. 14, No. 6, 469–477, (1996).

Ahmad, J., et al., "Evaluation of a Modified–Live Virus Vaccine Administered in ovo to Protect Chickens against Newcastle Disease", *Am. J. Vet. Res.*, 53, 1999–2004 (Nov. 1992).

Ahmad, J., et al., "Protection Against Hemorrhagic Enteritis and Newcastle Disease in Turkeys by Embryo Vaccination with Monovalent and Bivalent Vaccines", *Avian Dis.*, 37, 485–491 (1993).

Andre, F.E., "Development of Combined Vaccines: Manufactures' Viewpoint", *Biologicals*, 22, 317–321 (1994).

Calnek, B.W., et al., "Marek's Disease", In: *Diseases of Poultry*, 10th Edition, Calnek, B. W., et al., (eds.), Iowa State University Press, Ames, Iowa, USA, 369–413 (1997).

Clemens, J., et al., "Interactions Between PRP–T Vaccine against *Hemophilus Influenzae* Type b and Conventional Infant Vaccines", In: *Combined Vaccines and Simultaneous Administration*, Williams, J. C., et al., (eds.), The New York Academy of Sciences, New York, 255–266 (1995).

Goldenthal, K.L., et al., "Overview—Combination Vaccines and Simultaneous Administration", In: *Combined Vaccines and Simultaneous Aministration*, Williams, J. C., et al., (eds.), The New York Academy of Sciences, New York, xi–xv (1995).

Hadler, S.C., "Cost Benefit of Combining Antigens", *Biologicals*, 22, 415–418 (1994).

Insel, R.A., et al., "Potential Alterations in Immunogenicity by Combining or Simultaneously Administering Vaccine Components", In: *Combined Vaccines and Simultaneous Administration*, Williams, J. C., et al., (eds.), The New York Academy of Sciences, New York, 35–47 (1995).

Sharma, J.M., et al., "Comparative Viral, Immunologic, and Pathologic Responses of Chickens Inoculated with Herpesvirus of Turkeys as Embryos or at Hatch", *Am. J. Vet. Res.*, 45, 1619–1623 (Aug. 1984).

Sharma, J.M., et al., "Delayed Replication of Marek's Disease Virus Following in ovo Inoculation During Late Stages of Embryonal Development", *Avian Dis.*, 31, 570–576 (1987).

Sharma, J.M., et al., "Embryo Vaccination against Marek's Disease with Serotypes 1, 2 and 3 Vaccines Administered Singly or in Combination", *Avian Dis.*, 27, 453–463 (1983).

Sharma, J.M., et al., "Embryo Vaccination of Chickens with Turkey Herpesvirus: Characteristics of the Target Cell of Early Viral Replication in Embryonic Lung", *Avian Pathology*, 16, 567–579 (1987).

(List continued on next page.)

*Primary Examiner*—Michael P. Woodward
*Assistant Examiner*—Mary K Zeman
*Attorney, Agent, or Firm*—Schwegman, Lundberg, Woessner & Kluth, P.A.

[57] ABSTRACT

A multivalent poultry vaccine is provided having two or more live biological agents or microbial components. Each live biological agent or microbial component is effective in preventing or treating an avian disease, and the multivalent vaccine is safe and effective for immunizing poultry in ovo. Methods are also provided for vaccinating poultry by administering such a multivalent vaccine in ovo.

21 Claims, No Drawings

OTHER PUBLICATIONS

Sharma, J.M., et al., "Embryo Vaccination with Infectious Bursal Disease Virus Alone or in Combination with Marek's Disease Vaccine", *Avian Dis.*, 29, 1155–1169 (1985).

Sharma, J.M., et al., "Response of 18–Day–Old Chicken Embryos to an in ovo Newcastle Disease Vaccine", *Advances in Avian Immunology Research,* Davison, T. F., et al., (eds.), Carfex International Periodical Publishers, 273–277 (1994).

Wakenell, P.S., et al., "Chicken Embryonal Vaccination with Avian Infectious Bronchitis Virus", *Am. J. Vet. Res.,* 47, 933–938 (Apr., 1986).

Wakenell, P.S., et al., "Embryo Vaccination of Chickens with Infectious Bronchitis Virus: Histologic and Ultrastructural Lesion Response and Immunologic Response to Vaccination", *Avian Dis.,* 39, 752–765 (1995).

MULTIVALENT IN OVO AVIAN VACCINE

BACKGROUND OF THE INVENTION

Domestic Avian Diseases

Commercial chicken flocks in most parts of the world are routinely vaccinated to protect them against environmental exposure to pathogens. Some of the more common viruses that cause disease in domestic poultry include Marek's disease virus (MDV), infectious bursal disease virus (IBDV), Newcastle disease virus (NDV), infectious bronchitis virus (IBV), infectious laryngotracheitis virus (ILTV), avian encephalomyelitis (AEV), chick anemia virus (CAV), Fowlpox virus (FPV), avian influenza virus (AIV), reovirus, avian leukosis virus (ALV), reticuloendotheliosis virus (REV), avian adenovirus and hemorrhagic enteritis virus (HEV). These diseases are of economic importance to the poultry industry. Currently, vaccines are available to protect commercial poultry against most of these diseases. (*Diseases of Poultry*, 10th ed. (Calneck et al., eds.), Iowa State University Press, Ames, Iowa (1997)).

One of the most economically important diseases is Marek's disease (MD). MD is a lymphoproliferative disease that occurs naturally in chickens. The disease is caused by a herpesvirus that is extremely contagious, spreads horizontally, and has been responsible for major economic losses to the poultry industry. Chickens have sensitivity to this virus with no influence of lineage or sex, but it is reported that younger chickens have a higher sensitivity and suffer greater damage from the virus. The symptoms of MD appear widely in the nerves, genital organs, internal organs, eyes and skin of the infected birds causing motor trouble due to paralysis when the nerves have been affected, functional trouble of the internal organs due to tumors, and chronic undernourishment if the internal organs are attacked by the virus. The chickens usually die. MD is one of the leading causes of economic losses in the poultry industry.

Post-hatch Vaccination

In most commercial flocks, newly hatched chicks are given certain vaccines parenterally at hatch. Because exposure to pathogens often occurs at a very young age, they often need to be vaccinated before they are placed in rearing or brooder houses. Such a vaccination scheme requires handling of individual birds and involves the possible risk of accidental self-injection. Another problem with this vaccination method is that the vaccines are not always effective. The young chicks may become exposed to a virulent form of a disease too soon after vaccination, i.e., before they have the opportunity to develop adequate protective immunity.

In ovo Vaccination

It has been shown that certain live viral vaccines can be administered in eggs before the birds hatch. This procedure is called "in ovo vaccination." The in ovo vaccinated birds develop resistance to the target disease. The exact mechanism by which embryonal vaccination results in increased resistance to challenge at hatch is not yet clear. The poultry industry in the U.S. and abroad has responded to the benefits of in ovo vaccination and this procedure is rapidly gaining popularity. Over seven billion birds receive vaccines yearly in the U.S. In 1994, about 30% of the U.S. commercial chicken population was vaccinated against MD by the in ovo procedure. In 1997, the figure has risen to over 75% or about 6.0 billion chickens.

It should be noted, that many vaccines used previously for hatched birds cannot be used for in ovo vaccination because the vaccine agents are pathogenic for the embryo. Late stage embryos are highly susceptible to infection with most vaccine viruses examined. Not all vaccine viruses that are non-pathogenic for newly hatched chicks are also safe for late-stage embryos. For instance, vaccine strains of IBV and NDV that are used routinely as neonatal vaccines in newly hatched chicks are lethal for embryos following in ovo inoculation. These viruses have been modified to render them safe for in ovo use. Currently only the MD vaccine is being administered in ovo.

Use of Inactivated vs. Live Vaccines

Oil-emulsion vaccines prepared with mineral oil are highly efficacious formulations used widely against poultry diseases in various monovalent and polyvalent forms. Mineral oil vaccines, however, cause excessive tissue reactions. Also, the oil persists too long, is practically non-digestible, and is considered carcinogenic. A 42 day holding period is required before slaughter of poultry if a mineral oil vaccine is administered. Animal and vegetable oil vaccines have been developed to replace mineral oil vaccines. However, these have also resulted in tissue reactions.

Live, also called infectious, viral vaccines contain attenuated or naturally non-pathogenic isolates of viruses. The vaccines do not, by themselves, cause disease. The immune response stimulated by live vaccines protects against virulent target viruses present in the environment. Adjuvants such as mineral oil are not needed with live vaccines.

Use of Single vs. Combined Vaccines

Combined or multivalent vaccines offer a number of obvious advantages over monovalent vaccines. One advantage of a multivalent vaccine is that fewer vaccine inoculations are required. A single preparation can be administered in one inoculation and is effective against several diseases. As the range of potential vaccines increases, the combination of vaccines becomes even more mandatory in order to minimize the number of inoculations. The decreased number of inoculations needed when vaccines are combined would likely lead to an increased compliance to the vaccination schedule. This in turn would likely lead to a resulting increase in vaccine coverage, which would ultimately lead to better disease control.

Additional advantages of combined vaccines are the reduced costs of storage, transport and administration since there are fewer vials, ampules, syringes and needles needed. Given the fact that on a worldwide basis more than 90% of the cost of vaccination is caused by such logistic costs, this advantage is certainly not negligible. Also, if several vaccines are combined, vaccine schedules and record keeping is simplified.

Problems with Combined Vaccines

An unexpected problem of combined vaccines is the recently identified negative influence that one vaccine may have on another in a combination vaccine. It has been found that when two existing vaccines are simply mixed, one or both may lose their potency (Andre, F. E., "Development of Combined Vaccines: Manufacturers' Viewpoint," Biologicals 22:317–321 (1994); Hadler, S. C., "Cost benefit of combining antigens," Biologicals 22:415–418 (1994); Goldenthal, K, L., et al., "Overview—Combination Vaccines and Simultaneous Administration. Past, Present, and Future." In: *Combined Vaccines and Simultaneous Administration. Current Issues and Perspectives* (Eds. Williams, J. C., et al.) The New York Academy of Sciences, New York, pp. 1 XI–XV (1995); Clemens, J., et al., "Interactions between PRP-T Vaccine against Hemophilus influenzae Type b and Conventional Infant Vaccines. Lessons for Future Studies of Simultaneous Immunization and Combined Vaccines," In: *Combined Vaccines and Simultaneous Administration. Current Issues and Perspectives* (Eds.

Williams, J. C., et al.) The New York Academy of Sciences, New York, pp. 255–266 (1995); Insel, R. A., "Potential Alterations in Immunogenicity by Combining or Simultaneously Administering Vaccine Component,". In: *Combined Vaccines and Simultaneous Administration. Current Issues and Perspectives* (Eds. Williams, J. C., et al.) The New York Academy of Sciences, New York, pp. 35–47 (1995)).

Unfortunately, it cannot always be predicted by the use of currently established potency tests in the laboratory whether individual vaccine components will retain their potency. Developing a multivalent vaccine can be as difficult as developing a new monovalent vaccine. For example, several independent studies reported that when the Hib vaccine is combined with a whole cell pertussis vaccine there is no interference between the two vaccines, but when the Hib vaccine is combined with acellular pertussis vaccines, there is a substantial loss of the Hib immunogenicity. It was shown that when Hib is combined with DTaP, it maintains its immunogenicity if given at separate sites, while the immunogenicity is 5–15 times lower when the vaccines are administered combined at the same site. This unexpected result confirms that combining two existing vaccines is not simple and often gives very unpredictable results that are not detected during the initial studies, but only after extensive clinical testing.

Trials have confirmed that there may not be a direct correlation between antibody titers and protection. This finding indicates that the antibody titers that are measured may not correlate with protective efficacy of vaccines, and therefore that any modification to the vaccine (for instance, the addition of another component to make a combination vaccine), may influence vaccine efficacy without changing the antibody titers.

Another major difficulty in the development of combined vaccines is the unexpectedly large cost of developing these combined vaccines (Andre, F. E., "Development of Combined Vaccines: Manufacuters' Viewpoint," Biologicals 22:317–321 (1994)). While a few years ago it was believed that combining two already existing vaccines would be a simple and inexpensive operation, it has become obvious that the development of a combination requires a long time and a budget which is often similar to that necessary for the development of a new vaccine.

Thus, there is an unmet need for "multivalent" vaccines, i.e. vaccines containing multiple agents, that can be administered to poultry in ovo.

SUMMARY OF THE INVENTION

The present invention provides a multivalent poultry vaccine comprising two or more live biological agents or microbial components. For example, the vaccine may comprise two live biological agents, or it may comprise two microbial components, or it may comprise one of each. Each live biological agent or microbial component used in the multivalent vaccine is effective in preventing or treating a different avian disease. The multivalent vaccine is safe and effective for immunizing poultry in ovo. The dosage of the vaccine can be readily determined by a clinician or veterinarian employing animal models or other test systems that are well known to the art.

The live biological agent can be a virus, a bacterium, a fungus or a parasite. Preferably, the live biological agent is an attenuated virus. The microbial component can be derived from a microbe of viral, bacterial, fungal or parasitic origin. The microbial component, for example, can be a microbial protein or other subunit, or a recombinant polypeptide including a microbial polypeptide or a fusion polypeptide. The microbial component is able to produce active immunity. As used herein, the term "recombinant" is intended to mean that the polypeptide (or protein) of the microbial component is obtained by the techniques of genetic engineering. For example, a protein may be isolated from a microorganism, such as a bacterial cell, that has been transformed using an appropriate vector with foreign DNA fragments obtained from the genome of a viral strain of interest. As one skilled in the art will understand, it is not necessary to use the entire protein. A unique peptide corresponding to a portion of the full protein can be used. The polypeptide or a recombinant in which there is a vector containing immunogenic genes of other agents is present in the vaccine in an amount sufficient to induce an immune response against relevant antigens and thus protect animals against the disease of interest.

The attenuated viruses that may be present in the multivalent vaccine preferably include MDV, IBDV, NDV, IBV, ILTV, AEV, CAV, FPV, AIV, avian reovirus, ALV, REV, avian adenovirus, HEV, and recombinants thereof. More preferably, the viruses MDV serotypes 1, 2 and 3, IBDV, IBV and possibly also a pox vector containing F and HN genes of the NDV.

The vaccine of this invention may be administered to any avian animal, whether domestic or wild. In particular, it may be administered to those that are commercially reared for meat or egg production. Without limitation thereto, exemplary avians include chickens, turkeys, geese, ducks, pheasants, quail, pigeons, ostriches and the like. Preferably, the avian species is a chicken or turkey. Birds which are reared in high density brooder houses, such as broiler and layer chickens, are especially vulnerable to environmental exposure to infectious agents and would largely benefit from pre-hatch vaccination.

The present invention also provides a method of vaccinating poultry by administering in ovo an effective immunity-producing amount of a live multivalent vaccine. The multivalent vaccine can be administered during the final quarter of the embryonal incubation period. Preferably, the vaccine contains MDV serotypes 1, 2 and 3 and IBDV (such as commercially available vaccines like Bursine II (BurII)). In addition to MDV serotypes 1, 2 and 3, and BurII, the vaccine may contain non-pathogenic strain of NDV or recombinant vaccines containing immunogenic genes from NDV. Alternatively, the vaccine may comprise HVT containing NDV genes and MDV genes, FPV containing ILTV, influenza virus, IBDV, or vectors containing other protective genes. For most common avian diseases, the known vaccines designed for post-hatch administration would be used in accordance with the inventive method, adjusting the dosage as necessary.

DETAILED DESCRIPTION

As discussed previously, one of the most prevalent and economically destructive diseases of the poultry industry is Marek's disease (MD). It has been found that the turkey herpesvirus (HVT) vaccine can be effective in preventing MD. This vaccine has been routinely inoculated into newly hatched chicks prior to their being placed in brooder houses. Although HVT vaccine is generally quite effective, on occasion inoculated flocks experience heavy MD losses. Several factors may be responsible for vaccine failure. Because vaccine protection is mediated via immune response, exposure to virulent MDV before the vaccine has had time to generate adequate immunity may result in clinical MD. Also, quantitative studies have shown that the protective efficacy of HVT vaccine, especially if the vaccine is cell-free, is compromised if the recipient chickens have anti-HVT antibodies. Because of wide use of HVT vaccine in breeding flocks, most commercial chicks hatch with such maternally derived antibodies.

Furthermore, the commonly used HVT vaccine has been found to offer poor protection against strains of MDV that are highly virulent and may be responsible for some of the MD loses in vaccinated flocks (Sharma, J. M., "Embryo Vaccination Against Marek's Disease with Serotypes 1, 2 and 3 Vaccines Administered Singly or in Combination," Avian Dis. 27:453–463 (1983); Calnek, B. W. and R. L. Witter, "Marek's Disease." In: *Diseases of Poultry*, 10th ed. (Calnek, B. W. et al. eds.), Iowa State University Press, Ames Iowa, USA. (1997)). Polyvalent vaccines containing two or three serotypes of the virus offer better protection against very virulent MDVs than the monovalent vaccines containing only HVT (Sharma, J. M., "Embryo Vaccination Against Marek's Disease with Serotypes 1, 2 and 3 Vaccines Administered Singly or in Combination," Avian Dis. 27:453–463 (1983); Calnek, B. W. and R. L. Witter, "Marek's Disease." In: *Diseases of Poultry*, 10th ed. (Calnek, B. W. et al. eds.), Iowa State University Press, Ames Iowa, USA. (1997)). It has been shown that MD vaccines can be injected into eggs during later stages of embryonation, i.e., at embryonation day (ED) 17–18.

Insofar as the mechanism for protection is dependent upon an immune response, the development of immunologic competence in the embryo is one of the critical determinative factors relating to the time of inoculation. As a general rule, this competence develops in the final quarter of the incubation period, before which the embryos are highly susceptible to harmful effects of the infectious agents. It has been found that if vaccination occurs prior to this stage, not only is the extent of protection in the neonate reduced, but also the vaccine may induce lesions in the embryo and/or extraembryonic membranes. For instance, prenatal chickens injected in earlier stages of development with HVT manifested an apparent immunosuppression and developed pathological lesions. While vaccination may be given anytime during the final 25% of the incubation period, it can be appreciated that the immunologic response is not immediate. For optimum protection of the hatchling, eggs should therefore be inoculated at least about 3–4 days prior to hatch. In the chicken, for example, this translates to injection by the seventeenth or eighteenth day of the 21-day incubation, corresponding to the time when embryonated eggs are routinely transferred to hatching trays. Injection could be conveniently combined with the transfer step.

Another critical consideration relating to the time frame for inoculation is the receptiveness of the inner egg structure to efficacious inoculation. The site of injection must either be within the region defined by the amnion, to include the amniotic or allantoic fluid, or else in the yolk sac. By the beginning of the fourth quarter of incubation, the amnion is sufficiently enlarged that penetration thereof is assured nearly all of the time when the injection is made from the center of the large end of the egg along the longitudinal axis. With a chicken egg in its eighteenth day of incubation, injection midway along, and perpendicular to, the longitudinal axis results in an amnion penetration frequency of about 80%, versus about 20% for the yolk sac or the embryo itself.

Also, by the final quarter, the embryo is sufficiently developed and differentiated that it can tolerate the inherent randomization in the actual site of injection with no significant adverse effect on the rate of hatchability or on vital functions. Moreover, at this stage of incubation, the embryo is consistently positioned in the egg such that entry from the center of the large end will predictably result in injection in the upper dorsal region of the prenatal chick. Insofar as the embryo is bathed in the amniotic fluid and proceeds to ingest it during the final few days of incubation, vaccinal infection is readily initiated when the amniotic fluid receives the injection. Similarly, vaccine injected into the yolk sac may infect the embryo during the yolk absorption process prior to hatch. Generally, the allantoic or amniotic region is the preferred site of injection for the reason that the yolk may carry maternal antibodies that would have the effect of partially neutralizing non-cell associated vaccines.

The mechanism of injection is not particularly critical provided that it does not unduly damage the tissues and organs of the embryo or the extraembryonic membranes surrounding it. A hypodermic syringe fitted with a needle of about #22 gauge is suitable for the purpose. A one to 1¼ inch needle when fully inserted from the center of the large end will penetrate the shell, the outer and inner shell membranes enclosing the air cell, and the amnion. Depending on the precise stage of development and position of the embryo, a needle of this length will terminate either in the fluid above the chick or in the chick itself. A pilot hole may be punched or drilled through the shell in order to prevent damaging or dulling of the needle. In an automated system, it is envisioned that a penetrating device, such as that taught by Miller (U.S. Pat. No. 4,040,388), would be effective. While it would not be desirable to apply heat to the needle as suggested therein to the extent of inactivating the vaccine or cooking any portion of the egg's interior, sterilization between injections would be beneficial in preventing cross-contamination. Cross-contamination can be avoided by high pressure jet injection as known in the art of en masse human inoculation. It is usually unnecessary to reseal the hole after injection, though paraffin or the like would be suitable for the purpose. An automated system suitable for the injection procedure is currently commercially available (INOVOJECT®, Embrex Inc.).

Pre-hatch vaccine administration does not adversely affect hatchability or survival of chicks. It effectively initiates early protective immunity while chicks are still in the eggs. It has been demonstrated that protection against single infectious diseases could be induced by injecting vaccines into late stage embryonated eggs (Sharma, J. M., "Embryo vaccination with infectious bursal disease virus alone or in combination with Marek's disease vaccine," Avian Dis. 29:1155–1169 (1985); Wakenell, P. S., and J. M. Sharma, "Chicken embryonal vaccination with avian infectious bronchitis virus," Am. J. Vet. Res. 47:933–938 (1986); Wakenell, P. S., et al., "Embryo vaccination of chickens with infectious bronchitis virus: Histologic and ultrastructural lesion response and immunologic response to vaccination," Avian Dis. 39:752–765 (1995); Ahmad, J., and Sharma, J. M., "Evaluation of a modified-live virus vaccine administered in ovo to protect chickens against Newcastle disease," Am. J. Vet. Res. 53:1999–2004 (1992); Ahmad, J., and Sharma, J. M., "Protection against hemorrhagic enteritis and Newcastle disease in turkeys by embryo vaccination with monovalent and bivalent vaccines," Avian Dis. 37:485–491 (1993)).

Exposure of embryonated eggs at ED16–18 with non-pathogenic strains of IBDV, NDV, and IBV resulted in active replication of the viruses in various embryonic tissues. Some viruses produced transient pathological lesions in the embryonic tissues. Cell culture attenuated IBV caused embryonic lesions (Wakenell, P. S., et al., "Embryo vaccination of chickens with infectious bronchitis virus: Histologic and ultrastructural lesion response and immunologic response to vaccination," Avian Dis. 39:752–765 (1995)).

The responses of embryos to HVT and MDV, two serologically related herpes viruses, varied. Following exposure to HVT at ED 17, the virus replicated extensively in the embryo, first reaching high titers in the embryonic lung and then spreading to other tissues (Sharma, J. M., et al., "Comparative viral, immunologic, and pathologic responses of chickens inoculated with herpes virus of turkeys as embryos or at hatch," Am. J. Vet. Res. 45:1619–123 (1984)). When single cell suspensions of lung tissue at the peak of infection were cultured in vitro, viral antigen could be visualized in sporadic adherent cells (Sharma, J. M., Embryo vaccination of chickens with turkey herpes virus: Characteristics of the target cell of early viral replication in embryonic lung," Avian Pathol. 16:567–579 (1987)).

The response of the late-stage embryo to MDV was quite different from the response to HVT. When MDV was injected in ovo at ED17, there was no evidence that the virus replicated in embryonic tissues. Extensive efforts to isolate the virus from embryos by cocultivation with permissive monolayers were unsuccessful (Sharma, J. M., "Delayed replication of Marek's disease virus following in ovo inoculation during late-stage of embryonal development," Avian Dis. 31:570–576 (1987)). Although it became undetectable, the virus persisted in the embryo because chicks hatching from virus injected eggs subsequently developed clinical MD and a majority died due to progressive tumors (Sharma, J. M., "Delayed replication of Marek's disease virus following in ovo inoculation during late-stage of embryonal development," Avian Dis. 31:570–576 (1987)).

The mechanism by which vaccines induce protection following in ovo inoculation is not known. Because most vaccine viruses replicate in the embryo, the viruses likely stimulate the immune system of the embryo and initiate a protective response before the chick hatches. When 18-day-old embryos were exposed to NDV, IgM-bearing cells proliferated in the spleen and cecal tonsils and some of these cells allowed specific surface binding of biotin-labeled virus thus indicating that the cells were committed to a NDV-specific immune response (Sharma, J. M., and Ahmad, J., "Response of 18-day-old chicken embryos to an in ovo Newcastle disease vaccine," Advances in Avian immunology Research, (Eds. Davison, T. F., et al.) Carfex International Periodical Publishers, pp. 273–277 (1994)). The kinetics of this response have not been carefully examined, nor is it proven that an embryonic immune response is a prerequisite in all cases for the protection of the hatched chicken.

Embryonal vaccination under the aforementioned conditions is characterized by a hatch rate comparable to untreated eggs. Any improvement in protection rate of prenatally inoculated chicks over post-hatch-inoculated chicks accordingly represents a positive improvement over the prior art. Resistance against MD of young birds from 18-day-vaccinated embryos challenged on the first 3 days post-hatch is up to about four times or more than that of birds vaccinated on the first day. The effect for later challenge is less dramatic in that the immune response in the 4- to 8-day-old chicks inoculated at hatch is roughly equivalent to that of the 1-day-old chick inoculated 3 days pre-hatch.

The following example is intended to illustrate but not limit the invention.

EXAMPLE

Multivalent Vaccine Containing Three Serotypes of Marek's Disease Virus and Infectious Bursal Disease Virus A multivalent vaccine (MV) was developed by combining four viruses into one preparation. The vaccine contained one isolate each of serotypes 1, 2, and 3 of Marek's disease virus (MDV) and an infectious bursal disease virus (IBDV). The viruses used were as follows:

MDV serotype 1: CVI988

MDV serotype 2: 301B

MDV serotype 3: HVT

IBDV: Bursine II

These viruses were provided as a gift from Solvay Animal Health. These viruses are also commercially available from other sources.

Commercially available specific-pathogen-free white Leghorn chicken eggs were used for in ovo vaccination. The vaccines were injected manually in eggs at about the 18th day of embryonation. A hole was punched on the large end of the eggs and the inoculum was deposited by inserting a #22 gauge, 1¼ inch needle through the hole. Vaccine-injected and diluent-injected eggs were placed in hatching trays. Hatched chicks were wing-banded and placed in isolators.

For conventional vaccination, each chick at hatching was inoculated with 0.2 ml of the vaccine subcutaneously at the back of the neck. The dose in plaque forming units (PFU) of vaccine was the same for both methods of vaccination. The dose per egg or chick was 1000 PFU of each of the Marek's disease virus serotypes and 1000 50% tissue culture infectious doses ($TCID_{50}$) of IBDV.

The hatchability of eggs in each group was recorded. Chicks in different groups were held in separate isolators through the duration of the experiments. MD challenge virus (strain RB1B, 500 PFU per bird) was inoculated intraperitoneally (I/P) at 7 days of age. The challenge was terminated at 7 weeks of age. IBDV challenge virus (strain IM, 500 $ELD_{50}$ per bird) was inoculated intra-ocularly (I/O) at 3 weeks of age. The challenge was terminated at 4 weeks of age. Embryonated chicken eggs injected with MV during late states of embryonation hatched normally. See Tables 1–3 below.

TABLE 1

Hatchability Results from Project Number 115-1

| Inoculum at ED18 | n | % hatchability |
|---|---|---|
| MDV 1, 2, 3[a] | 22 | 100 |
| Bur II[b] | 20 | 90 |
| MDV 1, 2, 3 + Bur II | 40 | 95 |
| None | 47 | 96 |

ED = embryonation day
[a]1000 PFU of each virus
[b]1000 $TCID_{50}$

TABLE 2

Hatchability Results from Project Number 115-2

| Inoculum at ED18 | n | % hatchability |
|---|---|---|
| MDV 1, 2, 3 | 24 | 96 |
| BurII | 24 | 96 |
| MDV 1, 2, 3 + BurII | 41 | 78 |
| None | 50 | 96 |

TABLE 3

Hatchability Results from Project Number 115-3

| Inoculum at ED18 | n | % hatchability |
|---|---|---|
| MDV 1, 2, 3 | 36 | 92 |
| Bur II | 19 | 79 |
| MDV 1, 2, 3 + BurII | 52 | 85 |
| None | 52 | 96 |

The chicks hatching from eggs injected with the multivalent vaccine were resistant to challenge with virulent MDV and IBDV. See Tables 4–6 below. Antibody levels against MDV and IBDV were comparable between groups receiving these viruses singly or in combination. The antibody data showed that the immune systems of the birds hatching from eggs given multivalent vaccines were intact.

TABLE 4

Efficacy of multivalent vaccine containing MDV serotypes 1, 2 and 3 and IBDV
Proj. No.: 115-1

| Inoculation at ED18 | IBDV challenge response | | | | MDV challenge response | | |
|---|---|---|---|---|---|---|---|
| | Bur. | | | | | | |
| | Dead | Atr. in surv. | BI of surv. | % IBD | Dead | Dead + Lesions | % MD |
| MDV 1, 2, 3 | ND | ND | ND | ND | 0/16 | 0/16 | 0 |
| BurII | 0/20 | 3/20 | 4.1 | 15 | ND | ND | ND |
| MDV 1, 2, 3 + BurII | 0/20 | 5/20 | 4.1 | 25 | 0/15 | 0/15 | 0 |
| None | 15/23 | 8/8 | 2.4 | 100 | 18/19 | 19/19 | 100 |

ED = embryonation day
Bur. Atr. in surv. = gross bursal atrophy in survivors
BI of surv. = bursal index of survivors (bursa weight/body weight × 1000)
ND = not done

TABLE 5

Efficacy of multivalent vaccine containing MDV serotypes 1, 2 and 3 and IBDV
Proj. No.: 115-2

| Inoculation at ED18 | IBDV challenge response | | | | MDV challenge response | | |
|---|---|---|---|---|---|---|---|
| | Bur. | | | | | | |
| | Dead | atr. in surv. | BI of surv. | % IBD | Dead | Dead + Lesions | % MD |
| MDV 1, 2, 3 | ND | ND | ND | ND | 1/18* | 1/18 | 5 |
| BurII | 0/20 | 8/22 | 5.37 | 36 | ND | ND | ND |
| MDV 1, 2, 3 + BurII | 0/20 | 1/20 | 4.83 | 5 | 1/18 | 1/18 | 5 |
| None | 12/24 | 12/12 | 4.62 | 100 | 14/20 | 17/20 | 85 |

ED = embryonation day
Bur. Atr. in surv. = gross bursal atrophy in survivors
BI of surv. = bursal index of survivors (bursa weight/body weight × 1000)
ND = not done
*Died at week 6. Diagnosis based on gross lesions.

TABLE 6

Efficacy of multivalent vaccine containing MDV serotypes 1, 2 and 3 and IBDV
Proj. No.: 115-3

| Inoculation at ED18 | IBDV challenge response | | | | MDV challenge | | |
|---|---|---|---|---|---|---|---|
| | Bur. | | | | | | |
| | Dead | atrop in surv. | BI of surv. | % IBD | Dead | Dead + lesions | % MD |
| MDV 1, 2, 3 | ND | ND | ND | ND | — | 1/10 | — |
| BurII | 0/15 | 4/15 | 5.0 | 26.6 | ND | ND | ND |
| MDV 1, 2, 3 + BurII | 0/23 | 2/23 | 5.7 | 8.6 | 1/12 | 1/12 | 8.3 |
| None | 0/15 | 15/15 | 3.0 | 100 | 13/13 | 13/13 | 100 |

ED = embryonation day
Bur. Atr. in surv. = gross bursal atrophy in survivors
BI of surv. = bursal index of survivors (bursa weight/body weight × 1000)
ND = not done Although multivalent MDV+IBDV vaccines have been previously available for post-hatch use, the present invention is the first effective multivalent vaccine that is suitable for in ovo use. Further, the multivalent vaccine of the present invention contains all three serotypes of MDV, giving it a wider protective ability than a vaccine that has one or two of the serotypes missing.

All publications are incorporated by reference herein, as though individually incorporated by reference. The invention has been described with reference to various specific and preferred embodiments and techniques. However, it should be understood that many variations and modifications may be made while remaining within the scope of the invention.

I claim:

1. A multivalent poultry vaccine comprising two or more live biological agents, wherein each live biological agent is effective in preventing or treating an avian disease, wherein said multivalent vaccine prevents or treats two or more avian diseases including Newcastle disease and is safe for in ovo inoculation of poultry commercially reared for meat or egg production, and wherein the biological agent effective against Newcastle disease consists essentially of an avipox vector containing F and HN genes of Newcastle disease virus.

2. The multivalent vaccine of claim 1 wherein said avian species is selected from the group consisting of chicken, turkey, goose, duck, pheasant, quail, pigeon and ostrich.

3. The multivalent vaccine of claim 2 wherein said avian species is a chicken.

4. The multivalent vaccine of claim 2 wherein said avian species is a turkey.

5. The multivalent vaccine of claim 1 wherein said live biological agent is selected from the group consisting of a virus, bacterium, fungus or parasite.

6. The multivalent vaccine of claim 5 wherein said virus is an attenuated virus.

7. The multivalent vaccine of claim 6 wherein said virus is selected from the group consisting of Marek's disease virus (MDV), infectious bursal disease virus (IBDV), infectious bronchitis virus (IBV), infectious laryngotracheitis virus (ILTV), avian encephalomyelitis (AEV), chick anemia virus (CAV), Fowlpox virus (FPV), avian influenza virus (AIV), avian reovirus, avian leukosis virus (ALV), reticuloendotheliosis virus (REV), avian adenovirus and hemorrhagic enteritis virus (HEV) and recombinants thereof.

8. The vaccine of claim 6 wherein the vaccine contains MDV serotypes 1, 2 and 3 and IBDV.

9. The vaccine of claim 6 wherein the vaccine contains MDV serotypes 1, 2 and 3 and Bursine II (BurII).

10. The vaccine of claim 6 wherein the vaccine contains MDV serotypes 1, 2 and 3, BurII and an avipox vector containing F and HN genes of NDV.

11. The multivalent vaccine of claim 1 wherein said microbial component is derived from a microbe selected from the group consisting of a virus, bacterium, fungus or parasite.

12. The multivalent vaccine of claim 11 wherein said microbial component is derived from an attenuated virus.

13. The multivalent vaccine of claim 12 wherein said virus is selected from the group consisting of Marek's disease virus (MDV), turkey herpes virus (HVT), infectious bursal disease virus (IBDV), infectious bronchitis virus (IBV), infectious laryngotracheitis virus (ILTV), avian encephalomyelitis (AEV), chick anemia virus (CAV), Fowlpox virus (FPV), avian influenza virus (AIV), avian reovirus, avian leukosis virus (ALV), reticuloendotheliosis virus (REV), avian adenovirus and hemorrhagic enteritis virus (HEV) and recombinants thereof.

14. The vaccine of claim 12 wherein the vaccine contains MDV serotypes 1, 2 and 3 and IBDV.

15. The vaccine of claim 12 wherein the vaccine contains MDV serotypes 1, 2 and 3 and Bursine II (BurII).

16. The vaccine of claim 12 wherein the vaccine contains MDV serotypes 1, 2 and 3, BurII and an avipox vector containing F and HN genes of NDV.

17. A method of vaccinating poultry comprising administering in ovo to said poultry an effective immunity producing amount of the multivalent vaccine of claim 1.

18. The method of claim 17 wherein said multivalent vaccine is administered during the final quarter of the embryonal incubation period.

19. The method of claim 17 wherein the vaccine contains MDV serotypes 1, 2 and 3 and IBDV.

20. The method of claim 17 wherein the vaccine contains MDV serotypes 1, 2 and 3 and BurII.

21. The method of claim 17 wherein the vaccine contains MDV serotypes 1, 2 and 3, BurII and a pox vector vaccine containing F and HN genes of NDV.

* * * * *